US005702450A

United States Patent [19]

Bisserie

[11] Patent Number: 5,702,450
[45] Date of Patent: Dec. 30, 1997

[54] INTERVERTEBRAL DISK PROSTHESIS

[76] Inventor: Michel Bisserie, 54, rue du Faubourg Montmartre, Paris, France, 75009

[21] Appl. No.: 578,675

[22] PCT Filed: Jun. 27, 1994

[86] PCT No.: PCT/FR94/00774

§ 371 Date: Feb. 14, 1996

§ 102(e) Date: Feb. 14, 1996

[87] PCT Pub. No.: WO95/00082

PCT Pub. Date: Jan. 5, 1995

[30] Foreign Application Priority Data

Jun. 28, 1993 [FR] France .................... 93 07855

[51] Int. Cl.[6] .................................................. A61F 2/44
[52] U.S. Cl. .................................................. 623/17
[58] Field of Search .................................................. 623/17

[56] References Cited

U.S. PATENT DOCUMENTS

| 3,867,728 | 2/1975 | Stubstad et al. | 623/17 |
| 4,772,287 | 9/1988 | Ray et al. | 623/17 |
| 4,834,757 | 5/1989 | Brantigan | 623/17 |
| 5,071,437 | 12/1991 | Steffee | 623/17 |
| 5,458,638 | 10/1995 | Kuslich et al. | 623/17 |
| 5,522,899 | 6/1996 | Michelson | 623/17 |

FOREIGN PATENT DOCUMENTS

| 0 392 076 | 10/1990 | European Pat. Off. . |
| 1122634 | 9/1956 | France . |
| WO 90/11740 | 10/1990 | WIPO . |

*Primary Examiner*—Randy C. Shay
*Attorney, Agent, or Firm*—Young & Thompson

[57] ABSTRACT

An intervertebral disk prosthesis designed to replace at least partially an intervertebral disk which is composed of a left half-disk, and a right half-disk, each of the half-disks covering a half-disk surface. The prosthesis is at least one prosthetic member each of which having a rigid upper plate, a rigid lower plate, and an elastic cushion placed between the upper plate and the lower plate. The elastic cushion has an upper face attached to the upper plate and a lower face attached to the lower plate. Each prosthetic member covers no more than the half-disk surface so as to replace either or both of the left half-disk and the right half-disk.

9 Claims, 2 Drawing Sheets

INTERVERTEBRAL DISK PROSTHESIS

BACKGROUND OF THE INVENTION

1. Field of the Invention

This invention relates to an internal prosthesis for human use designed to replace a deficient intervertebral disk in the lower back, and particularly in the lumbar and lumbar-sacral regions.

2. Description of the Related Art

The general basic concern in osteoarticular surgery is to repair lesions and possibly to prevent their aggravation, in order to preserve the two functions (the support function and the movement function) of osteo-articular structures whenever possible.

The most frequent reason for surgery on the spinal column at the present time is mechanical deterioration of intervertebral support structures, the most important of which is the intervertebral disk.

Evolution of this deterioration usually has two harmful consequences:

firstly pain, and limitations of movement capabilities in the spinal column itself;

secondly, deterioration of neurological structures contained in the spinal canal by mechanical compression, which causes peripheral deficiencies.

Vertebral surgery therefore attempts to satisfy three objectives in these cases:

1) restore the support function of the intervertebral structures;

2) restore the movement function of these structures;

3) release neurological structures for which the integrity may have been adversely affected.

With current surgical techniques, it is impossible to satisfy these three objectives using a single operating procedure, due to the specific anatomic configuration of the spinal column.

firstly, it is usually only possible to satisfactorily treat neurological lesions by a posterior surgical approach, in which case only palliative actions can be done on the intervertebral disk which will remain deficient, or the disk can be completely eliminated by fusing the vertebra by bone grafts which will provide support but which will permanently eliminate movement;

secondly, and up to this day, the only way of replacing the intervertebral disk by a mobile prosthesis is to use an anterior surgical approach in which it is usually impossible to satisfactorily treat posterior neurological lesions mentioned above at the same time.

Disk prostheses known at the present time provide total and single-piece disk replacement, which is technically only possible by an anterior approach.

Furthermore, current disk prostheses restrict movements and do not have all mechanical properties necessary to enable all desireable mobilities in the three planes in space and their combinations necessary for physiological functioning of an intervertebral stage.

The concept of making prostheses, for example disk prostheses containing a flexible insertion part placed between two rigid disks (patent FR-1,122,634) was introduced a few decades ago.

Furthermore, in order to avoid these disadvantages, Dr. Arthur D. STEFFEE, M.D., designed a prosthesis which had a mechanical structure capable of restoring support and all physiological disk movements at the same time (EP-0.392.076). This was a remarkable improvement.

However once again, this equipment can only be installed by an anterior surgical approach and is only designed for complete replacement of a disk as a single part. To our knowledge at the present time, this product has not been made available to surgeons.

SUMMARY OF THE INVENTION

The prosthesis according to the invention can remedy these disadvantages. Its appropriate structure, shape and dimensions are designed so that a half-disk can be replaced by a prosthetic part.

This makes it possible to achieve the three objectives mentioned above (restore the support function, restore the movement function and release neurological structures) in a single posterior surgical approach and in a single operation, possibly using two symmetrical prostheses in order to replace an entire disk.

Consequently, the invention relates to an intervertebral disk prosthesis designed to be placed in the disk space containing an upper rigid plate, a lower rigid plate, an elastic cushion placed between the upper plate and the lower plate, and comprising an upper face and a lower face, each being fixed to the corresponding plate.

The intervertebral disk prosthesis according to the invention comprises at least one prosthetic member, constituting a fraction of a disk, corresponding at most to half a disk.

In a preferred embodiment, it is formed of two disk fractions each forming a half-prosthesis.

This prosthesis can be inserted by a posterior approach through the spinal canal, which is a major advantage of the invention in surgical practice.

There is no mechanical disadvantage in using two prosthetic half-disks when a disk is to be replaced provided that dimensions are judiciously chosen, and precise positioning will enable the two contiguous half-prostheses to work synchronously, forming the mechanical equivalent of a single piece disk unit.

Furthermore in some cases, use of a single half-prosthesis may be preferred, conserving the other half of the natural disk if its condition is still considered to be compatible with satisfactory function which, in any case, will be assisted by the half-prosthesis.

When this seems feasible, the operation can thus be simplified.

This type of partial disk replacement may be indicated particularly:

in case of asymmetric deterioration of a disk, with the disk being compressed on one side;

in some scoliotic deformations in which the judicious use of a half-prosthesis at one or more than one level could rebalance the vertebral curvature while maintaining function.

It has the following useful characteristics, possibly combined depending on which combinations are technically possible:

its global parallelepiped shape and appropriate dimensions enable surgical insertion by posterior approach through the spinal canal;

the plates are made of a biocompatible material and are approximately rectangular;

each plate has a ledge type relief on its external face, precisely oriented so as to prevent displacement of the prosthesis along a specific direction after its installation;

3 the external surface of the plates between the ledge patterns is rough and has sharp edges to enable bone rehabitation from the vertebral bone surfaces against which it is applied during surgical implantation;

the edges of the plates are rounded at each side, and within the thickness;

extraction notches are formed in the plates;

the cushion is a laminated composite elastic material, or is made of silicone or a product in the polyolefines family.

Complete replacement of a disk is not systematically necessary depending on each pathological case encountered, but when it is necessary it will be facilitated by symmetric insertion of two half-disk prostheses at the stage being operated on, one on the right side and the other on the left side of the intervertebral space considered.

BRIEF DESCRIPTION OF THE DRAWINGS

A detailed description of the invention will be made with reference to the drawings in the appendix, in which.

DESCRIPTION OF THE PREFERRED EMBODIMENT

Figure 2:
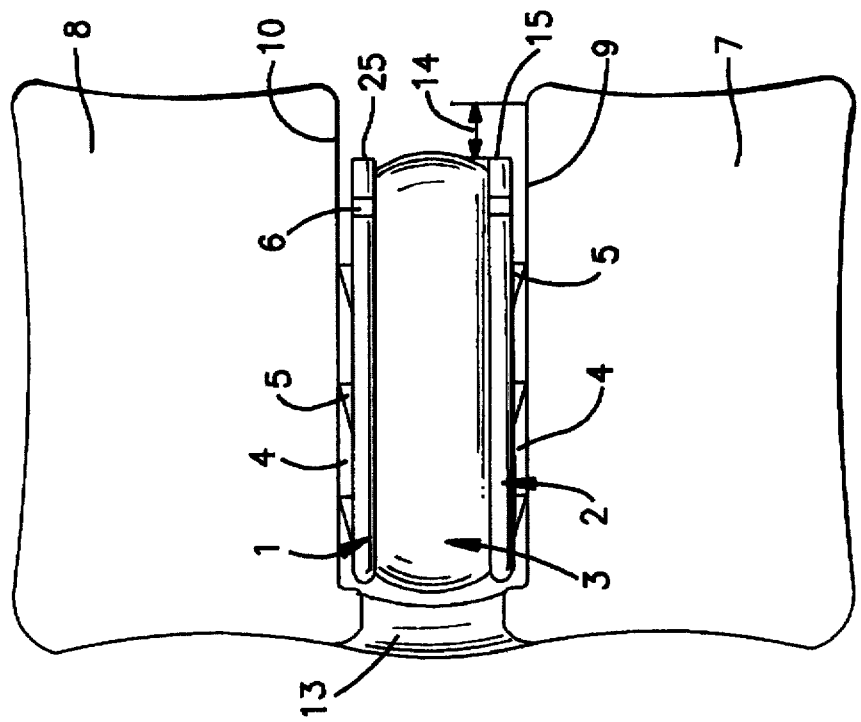
FIG. 2 shows a sagittal section through the prosthesis in position between two vertebral bodies.
Figure 1:
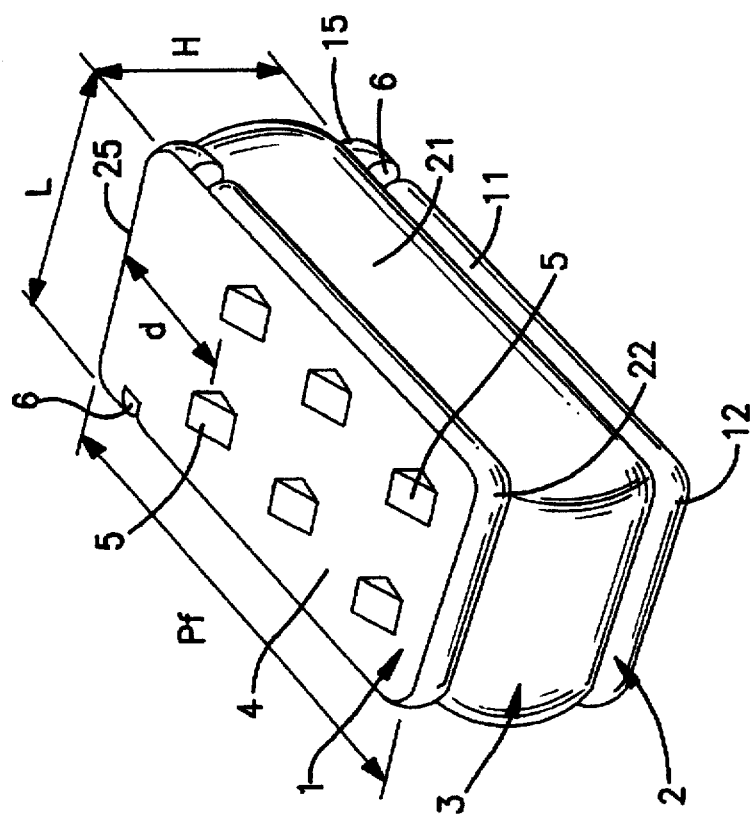
FIG. 1 shows a ¾ perspective overall view of the front of a prosthesis according to the invention.

Posterior bone, ligament and neurological structures are omitted on FIG. 2.

The upper metal plate 1 and lower metal plate 2 are composed of a biocompatible metal already tested in the field of orthopedic surgery.

Their radio-opaqueness is a major advantage for post-operation monitoring of the position and behavior of the prosthesis.

In one specific embodiment, they may be made of titanium which is particularly useful in that this material is radio-opaque and is also compatible with carrying out nuclear magnetic resonance examinations, which is very useful if post-operational endo-spinal canal explorations are necessary.

It is beneficial if the peripheral surfacing of these metal plates is cast as a single piece. This provides two advantages:

surface irregularities 4 encourage rehabitation by bone tissue;

ledge shaped relief structures 5, which we will call "anti-withdrawal ledges", which are oriented so as to prevent secondary migration of the prosthesis from the front towards the back, in other words from the intervertebral space towards the vertebral canal and the neurological structures contained in it.

These two surface properties of the metal plates contribute to the stability of the prosthesis when in position, firstly by an immediate grip during installation, and secondly eventually through bone rehabitation.

The drawings in the appendix show three sets of two ledges on each metal plate distributed over the surface of the metal plate, but this example is not restrictive.

However, the line at which the first ledges are positioned is at a distance d from the posterior edge of the metal plate allowing the use of a specific supporting device used for initial positioning of the prosthesis between vertebral bodies. A distance d=7 mm is satisfactory.

4

The plates can also be composed, for example, of a biocompatible carbon-graphite type of composite material with the same morphological characteristics.

Furthermore, rigid plates 1, 2 have rounded edges 11, 21 and rounded corners 12, 22 (foam) at the front in order to limit the risk of traumatism of nearby anatomic structures when placing the prosthesis; this risk would be much too high if the corners and edges were sharp.

The rear surfaces 15 and 25 are straight, to facilitate inserting the prosthesis using the supporting device that bears on these surfaces.

Notches, called extraction notches 6, are formed in the metal of each rigid plate, towards the posterior part of its edges.

These notches 6 are used to exert a backwards tension on the prosthesis using an appropriate instrument, if another surgical operation is necessary at a later date in which ablation of the prosthesis is necessary.

The elastic cushion 3 is formed of a disk material with mechanical properties as similar as possible to the properties of a natural disk, in other words it must satisfy the requirements of physiological stresses with elasticity and strength properties as a function of the compression, tension and shear forces, both in rotation and in sliding.

These mechanical properties have been defined using a great deal of experimental data determined from well known and reputable biomechanical work done on human anatomy parts.

The result is that the prosthetic disk material is made either of a silicone type elastomer, or of a laminated composite material or of an elastic material in the polyolefines family.

The prosthesis according to the invention is designed to correct the deficiencies of an intervertebral disk in as many pathological configurations as possible.

It will preferably be used in the lumbar part of the spinal canal and the design of the prosthesis is such that it can be placed at this lumbar level preferably by a posterior approach through the spinal canal, this type of approach making it possible to treat posterior lesions in the spinal column and to do a disk replacement in, a single surgical operation.

Each prosthesis according to the invention is designed to replace half of a lumbar disk, from the right or from the left it replaces a fraction of a disk covering not more than half of the surface of the disk space.

Figure 3:
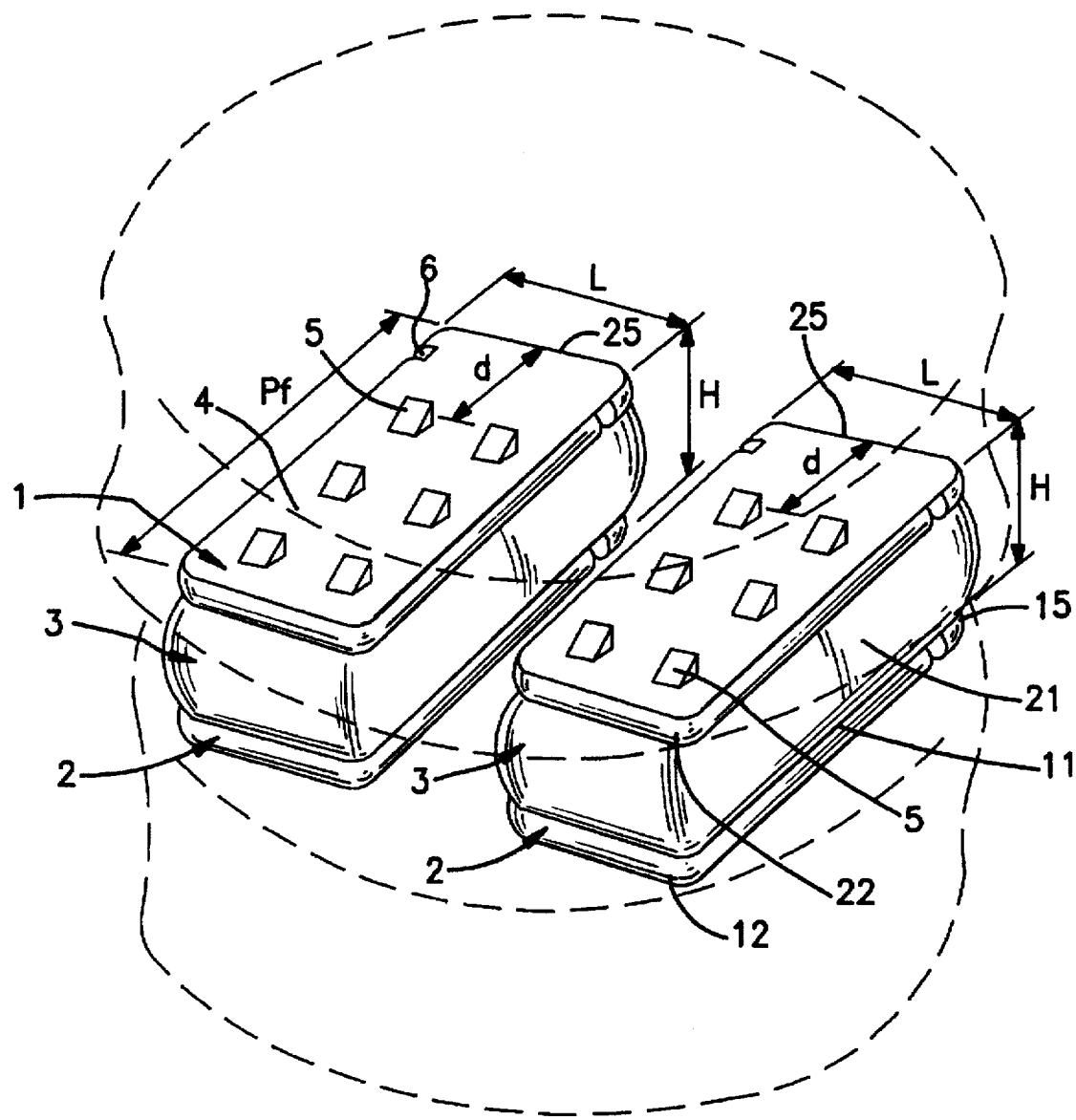
FIG. 3 shows an arrangement of two of the devices in position between two vertebral bodies.

If necessary, and depending on disk lesions diagnosed and then observed during the operation, the two prostheses can be implanted, one from the right and one from the left in the same intervertebral stage, so as to perform a complete disk replacement, as shown in FIG. 3.

This placement using a posterior approach requires sufficient widening of the bone canal to give a good exposure area and to provide good protection of nearby neurological structures.

The prosthesis according to the invention is inserted between the vertebral bodies after appropriate discectomy by preparing a site between vertebra by recessing the vertebral plates using a special instrument.

FIG. 2 shows a sagittal section of a prosthesis according to the invention in position between two vertebral bodies 7 and 8 with its attachment devices 4, 5, at the prepared vertebral bone surfaces 9, 10, and shows the desirable preservation of an anterior peripheral part of the disk annulus 13, with an anterior-posterior thickness of the order of 2 to 4 mm.

Furthermore, the intersomatic recess and the dimensions of the prosthesis are calculated as a function of the anatomic characteristics of the case being operated, in order to create a safety space 14 of at least 3 mm between the vertical line in the vertebral canal (posterior edge of vertebral bodies) and the posterior part of the prosthesis in position.

This ensures that the prosthetic equipment does not project into the canal.

A wide range of sizes of the prosthesis according to the invention are provided with variations in all three dimensions, so that said prosthesis can be used in different pathological cases, for different anatomic configurations and at different lumbar intervertebral levels.

We have created the following variations as a result of practical operating experience in placing intersomatic grafts using the same method, but these examples are not restrictive:

it is designed with two different depths Pf; one equal to 25 mm and the other equal to 30 mm;

in each of these two depth categories, there will be variations in the height H and width L of the prosthesis;

for each of the two depths considered, the height H may vary from 9 to 13 millimeters, in steps of one millimeter;

for each defined depth and each height, the width L may vary from 9 to 12 millimeters, in steps of one min.

The advantages of using the prosthesis according to the invention for the dorsal spinal column may be very limited for two reasons:

firstly, due to the lack of natural physiological mobility of this thoracic segment;

secondly, due to difficulties and dangers inherent to the presence of the spinal chord which is no longer present at the lumbar level.

However, it may be useful and it is possible to use the prosthesis according to the invention for the lower dorsal segments D11–D12 and D12–L1, for which restoration of mobility may be useful in some pathological cases.

Reference signs inserted after the technical characteristics mentioned in the claims are given only to facilitate understanding of the claims, and in no way restrict the scope.

I claim:

1. Intervertebral disk prosthesis designed to replace at least partially an intervertebral disk which is composed of a left half-disk and a right half-disk, each of said half-disks being sized to cover a half disk surface, said prosthesis including at least one prosthetic member, each of said at least one prosthetic member comprising a rigid upper plate, a rigid lower plate, an elastic cushion placed between the upper plate and the lower plate and containing an upper face attached to said upper plate and a lower face attached to said lower plate, and each of said at least one prosthetic member being sized to cover no more than said half-disk surface so as to replace one of said left half-disk and said right half-disk, wherein rear edges of said upper plate and said lower plate are straight and remaining edges of the upper plate and the lower plate are rounded at each side, and within their thickness.

2. Intervertebral disk prosthesis according to claim 1, wherein said prosthesis has a parallelepiped shape which enables surgical insertion by posterior approach through a spinal column.

3. Intervertebral disk prosthesis according to claim 1, wherein said upper plate and said lower plate are each substantially rectangular.

4. Intervertebral disk prosthesis according to claim 1, wherein each of said upper plate and said lower plate comprises at least one wedge shaped structure (5) on an external face oriented to prevent movement of the prosthesis in a specific direction after installation of said prosthesis.

5. Intervertebral disk prosthesis according to claim 4, wherein the external face (4) of each of said upper plate and said lower plate (1, 2) surrounding said at least one wedge shaped structure (5) is rough and has sharp edges facilitating bone rehabitation from vertebral bone surfaces against which said external faces are applied during the surgical implantation.

6. Intervertebral disk prosthesis according to claim 1, wherein said upper plate and said lower plate comprise extraction notches (6).

7. Intervertebral disk prosthesis according to claim 1, wherein the elastic cushion (3) is made of a laminated composite elastic material.

8. Intervertebral disk prosthesis according to claim 1, wherein the cushion (3) is made of silicone or a product in the polyolefins family.

9. Intervertebral disk prosthesis according to claim 1, wherein said prosthesis is formed of two prosthetic members, one of said two prosthetic members corresponding to said left half-disk and another of said two prosthetic members corresponding to said right half-disk.

* * * * *